United States Patent [19]

Choi

[11] Patent Number: 5,487,877

[45] Date of Patent: Jan. 30, 1996

[54] RESTROOM ORGANIZER AND STERILIZING APPARATUS

[76] Inventor: Min K. Choi, 14525 Memorial Dr., Houston, Tex. 77079

[21] Appl. No.: 256,990

[22] PCT Filed: Feb. 1, 1993

[86] PCT No.: PCT/US93/00885

§ 371 Date: Jul. 29, 1994

§ 102(e) Date: Jul. 29, 1994

[87] PCT Pub. No.: WO93/14668

PCT Pub. Date: Aug. 5, 1993

[30] Foreign Application Priority Data

Feb. 1, 1992 [KR] Rep. of Korea .............................. 1590
Jul. 1, 1992 [KR] Rep. of Korea ............................ 11676
Sep. 29, 1992 [KR] Rep. of Korea ............................ 18525

[51] Int. Cl.$^6$ ............................ A45D 34/06; A61L 2/10; A61L 2/24

[52] U.S. Cl. ............................. 422/300; 422/24; 222/52; 222/192; 250/455.11

[58] Field of Search ............................. 422/24, 116, 300, 422/22, 28, 307; 222/52, 192; 250/455.11; 206/209.1, 362.1, 362.2

[56] References Cited

U.S. PATENT DOCUMENTS

| | | | |
|---|---|---|---|
| 1,845,291 | 2/1932 | Koontz | 222/102 |
| 2,245,762 | 6/1941 | De Stefani et al. | 422/24 |
| 2,528,662 | 11/1950 | Miller | 222/101 |
| 2,563,733 | 8/1951 | Meczelski | 222/102 |
| 2,587,131 | 2/1952 | Ficken | 206/209.1 |
| 2,592,131 | 4/1952 | Farrar | 250/455.11 |
| 2,596,683 | 5/1952 | Hawkins | 222/101 |
| 3,100,842 | 8/1963 | Tellefsen | 250/455.11 |
| 3,114,038 | 12/1963 | Meader | 250/454.11 |
| 3,198,389 | 8/1965 | Dunning | 222/93 |
| 3,313,454 | 4/1967 | Welsh et al. | 222/102 |
| 3,353,905 | 11/1967 | Ellis | 422/291 |
| 3,741,378 | 6/1973 | Parker | 206/209 |
| 3,820,251 | 6/1974 | Abernathy | 34/60 |
| 3,860,147 | 1/1975 | Vessio et al. | 222/96 |
| 3,867,096 | 2/1975 | Doucette | 422/99 |
| 3,881,868 | 5/1975 | Duke | 206/209.1 |
| 3,884,635 | 5/1975 | Sloan | 206/209.1 |
| 3,955,922 | 5/1976 | Moulthrop | 422/300 |
| 4,214,657 | 7/1980 | Winston | 206/209.1 |
| 4,234,104 | 11/1980 | Apuzzo et al. | 222/94 |
| 4,258,864 | 3/1981 | Karamanolis et al. | 222/96 |
| 4,403,714 | 11/1983 | Kane | 222/101 |
| 4,421,252 | 12/1983 | Ylitalo | 222/102 |
| 4,473,152 | 11/1984 | Jump et al. | 206/209.1 |
| 4,508,242 | 4/1985 | Wolfe | 222/102 |
| 4,625,119 | 11/1986 | Murdock, III | 250/455.11 |
| 4,629,095 | 12/1986 | Smith | 222/96 |
| 4,740,706 | 4/1988 | Murdock, III | 250/455.11 |
| 4,806,770 | 2/1989 | Hylton et al. | 250/455.11 |
| 4,915,219 | 4/1990 | Ottimo | 206/209.1 |
| 4,921,150 | 5/1990 | Lagergren et al. | 222/639 |
| 4,938,384 | 7/1990 | Pilolla et al. | 222/52 |
| 4,950,902 | 8/1990 | Ritter | 250/455.11 |
| 4,973,847 | 11/1990 | Lackey et al. | 250/455.11 |
| 4,995,509 | 2/1991 | Kornfeind | 206/209.1 |
| 5,023,460 | 6/1991 | Foster et al. | 250/455.11 |
| 5,050,773 | 9/1991 | Choi | 222/63 |
| 5,086,916 | 2/1992 | Gray | 206/209.1 |
| 5,120,499 | 6/1992 | Baron | 250/455.11 |
| 5,126,572 | 6/1992 | Chu | 250/455.11 |
| 5,127,521 | 7/1992 | Bourque | 206/362.1 |
| 5,215,218 | 1/1993 | Choi | 222/63 |

FOREIGN PATENT DOCUMENTS

| | | |
|---|---|---|
| 2443975 | 8/1980 | France . |
| 2345650 | 3/1975 | Germany . |
| 2639991 | 3/1978 | Germany . |
| 2644151 | 4/1978 | Germany . |
| 3904143 | 8/1990 | Germany . |

*Primary Examiner*—Robert J. Warden
*Assistant Examiner*—Theresa T. Snider
*Attorney, Agent, or Firm*—Mark A. Oathout

[57] ABSTRACT

The present invention relates to a restroom organizer and toothbrush sterilizing apparatus (1) which includes a toothbrush sterilizer (4), a toothpaste dispenser (2) a soap supplier (7a) and a control circuit (11). Various sanitizers (4, 31, 80, 100) are disclosed for disinfecting and deodorizing various articles and of the atmosphere. The invention also discloses various compartments (40, 50, 82, 84) for storing items to be sanitized.

17 Claims, 15 Drawing Sheets

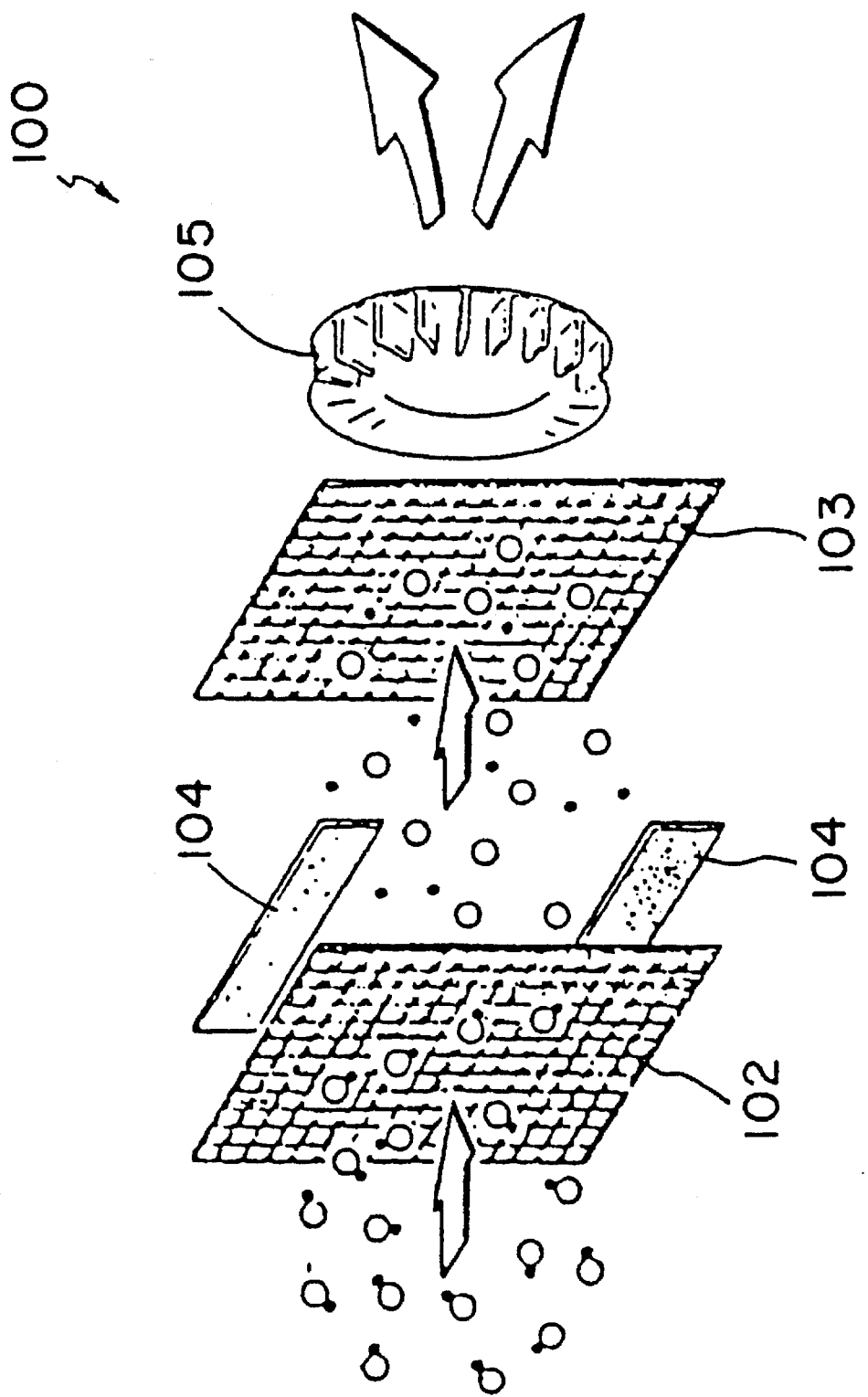

RESTROOM ORGANIZER AND STERILIZING APPARATUS

BACKGROUND

Several prior art sterilizers generally consist of an ultraviolet ray light or an infrared ray light sterilization system located at the upper part of the main block. These devices sterilize the objects through rays of light. Although, this is an effective means of sterilization, there are shortcomings such as the wasting of electricity by leaving lights on for long periods of time and the need to replace bulbs when a filament has burned out. The ozone sterilizing apparatus is designed to improve upon the shortcomings.

There are two kinds of prior art sterilizers, one for domestic use and another for professional use.

The prior art domestic sterilizer consists of a sterilizing light and is operated by a switch when it is needed. The prior art professional sterilizer is structured and used for a specific purpose. It is limited to sterilizing only specific items. For instance, a toothbrush sterilizer cannot be used for any other item except for a toothbrush, and the sterilizing light bulb which is the essential component stays on for an unnecessary length of time. Therefore, it wastes more electricity and shortens the light bulbs life.

SUMMARY OF THE INVENTION

This invention provides a restroom organizer which combines toiletries, various necessities and electric apparatus together to be used in a restroom in a more compact fashion.

There are many items which can be used to clean and make up an individual's body. These items are frequently spread around the restroom. For example, each individual takes his or her toothbrush from the storage case, gets the toothpaste from a separate tube, cleans their teeth and returns the tube and brush to their storage cases. Or, an individual may use an electric toothbrush in the restroom and set it on an electric charging apparatus out of the restroom if there is no facility in the bathroom. When an individual washes their hair they take the proper amount of shampoo from a bottle by turning the bottle up-side-down and then putting the bottle back in its place. After washing their hair the individual will go to the counter or sink to put lotions and other creams on their body. Thus, the various toilet necessities are spread about the bathroom and need to be arranged in a more compact manner. The purpose of this invention is to group these necessities into one automated compound or organizer. Another purpose of the invention is to build an organizer for electric devices which includes an AC-DC converter for an electric toothpaste dispenser, an electric toothbrush and its associated charging apparatus, a sterilizer, electric razor and its charging apparatus and a toiletry set and soap supplier. The system also includes an electric circuit for control of the organizer.

The sterilizer is designed to improve upon the above shortcomings. It turns on and off when the door is opened and closed and the sterilizing light turns on for a preset period of time. For example, the light can be designed to turn on for two minutes while the sterilization process is carried out with the music or a melody playing during this process. The sterilizer can also be designed to then turn off for example, for three minutes, and turn on, for example, for two minutes with the music on, and so on.

Other improvements in this invention over the prior art includes the storage case which stocks toothbrushes, razors, soaps and other necessities. The storage case can be rotated forward or backward and is replaceable with a second storage case designed to contain baby nipples and a baby bottle for an infant when they require sterilization.

Another improvement of this invention is that the sterilizer can be combined with other apparatuses. In other words, the sterilizer can be built as one compartment in the organizer, next to the toothpaste dispenser or it can built inside the toothpaste dispenser for combined use.

Another embodiment of the sterilizing invention generally comprises an improved toothbrush sterilizing apparatus having an ozone system built into a toothbrush storage compartment which sterilizes the toothbrush and gets rid of foul odors.

BRIEF DESCRIPTION OF THE DRAWINGS

FIG. 19. is an exploded view of the ozone apparatus.

DETAILED DESCRIPTION

Figure 1:
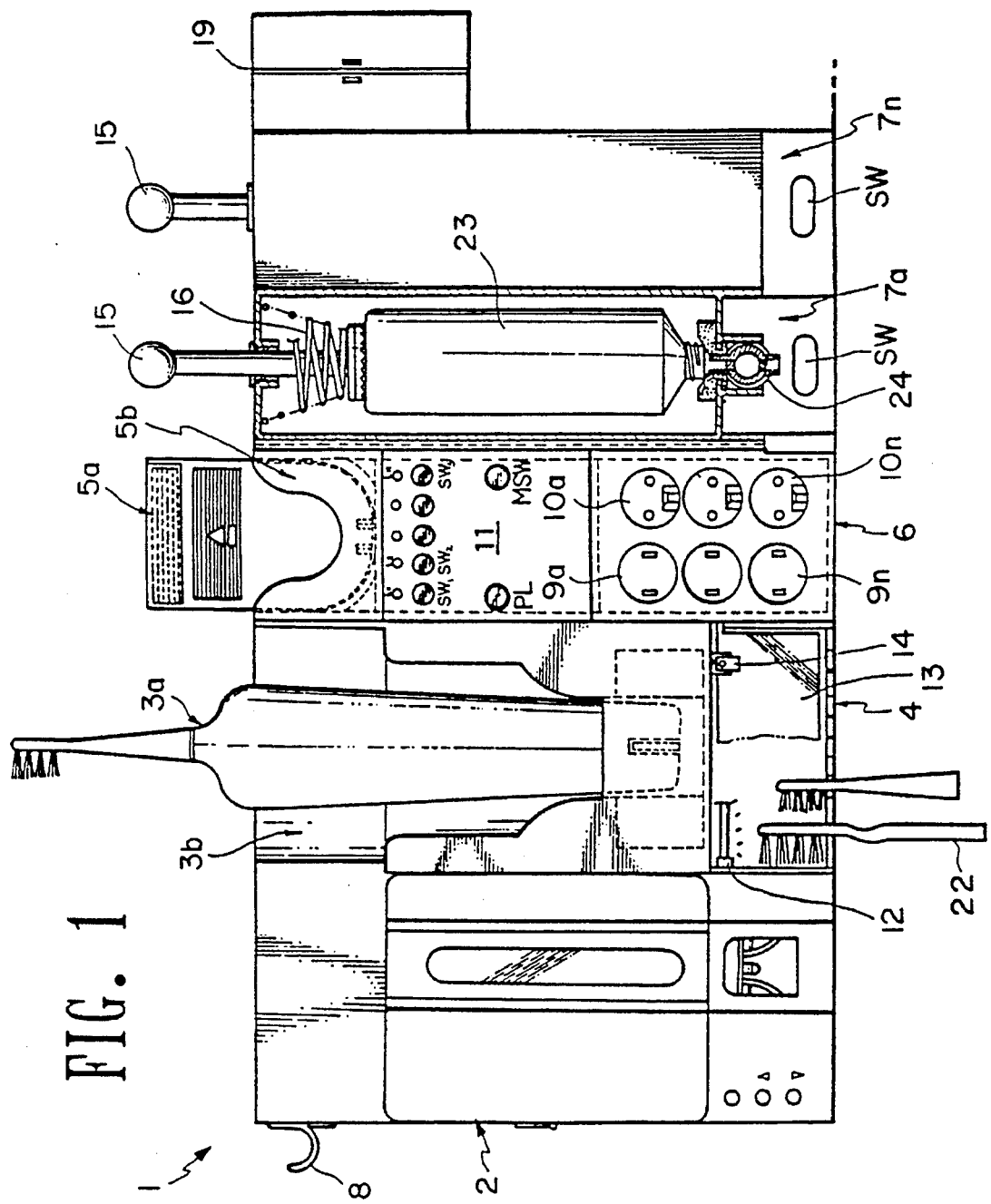
FIG. 1 is a front elevational view of the restroom organizer invention.

Referring to FIG. 1 the automated bathroom organizer or compound 1 is shown. This organizer 1 includes an AC-DC converter 21 (FIG. 4), an electric toothpaste dispenser 2, an electric toothbrush 3a and its electric charging apparatus 3b, a toothbrush sterilizer 4, an electric razor 5a and its electric charging apparatus 5b, a 110V/220V concentre 6, a toiletry set and soap supplier compartment 7a through 7n, store room 19 and a central electric circuit 11 to control the apparatus. The organizer 1 has one or more hanging hooks 8 for hanging a hair dryer or other utensil.

Figure 3:
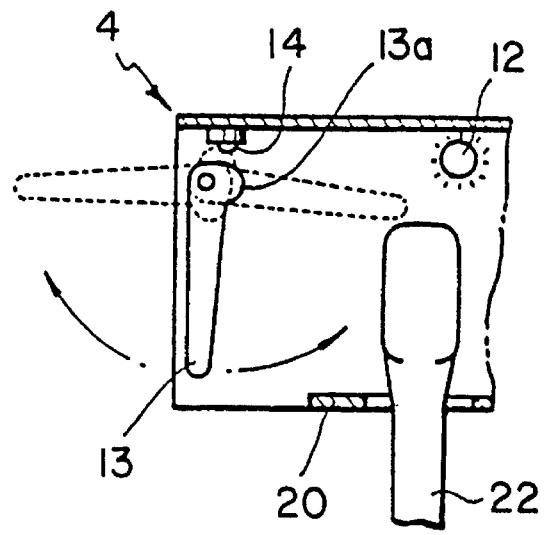
FIG. 3 is a partial section view of the ultraviolet sterilizer compartment.

Referring to FIG. 3 one embodiment of the toothbrush sterilizer 4 is shown. The sterilizer 4 includes brush holders 20, and ultraviolet sterilizing light 12, a perceive switch 14 which operates the sterilizing light 12 when a hanging toothbrush 22 is perceived to be hanging in the sterilizer 4 by a cover 13 which is built under the perceive switch 14 to turn on the sterilizer 4.

A user can pull out the toothbrush 22 which has been sterilized by ultraviolet rays and rotate cover 13 upward without touching the perceive switch 14. When the user pushes the cover 13 with the toothbrush 22 to hang it after use, then the spout 13a of the cover touches the perceive switch 14 to turn the ultraviolet light 12 on for a preset period of time. The light 12 turns off after the preset period of time has passed at which time the toothbrush 22 will be sterilized through the electric circuit 11.

As shown in FIG. 1 the electric concentre 6 includes a 110V concentre 9a–n and a 220V concentre 10a–n for selective use dependent upon the electric capacity of the item to be plugged in to one of the outlets.

Figure 2:
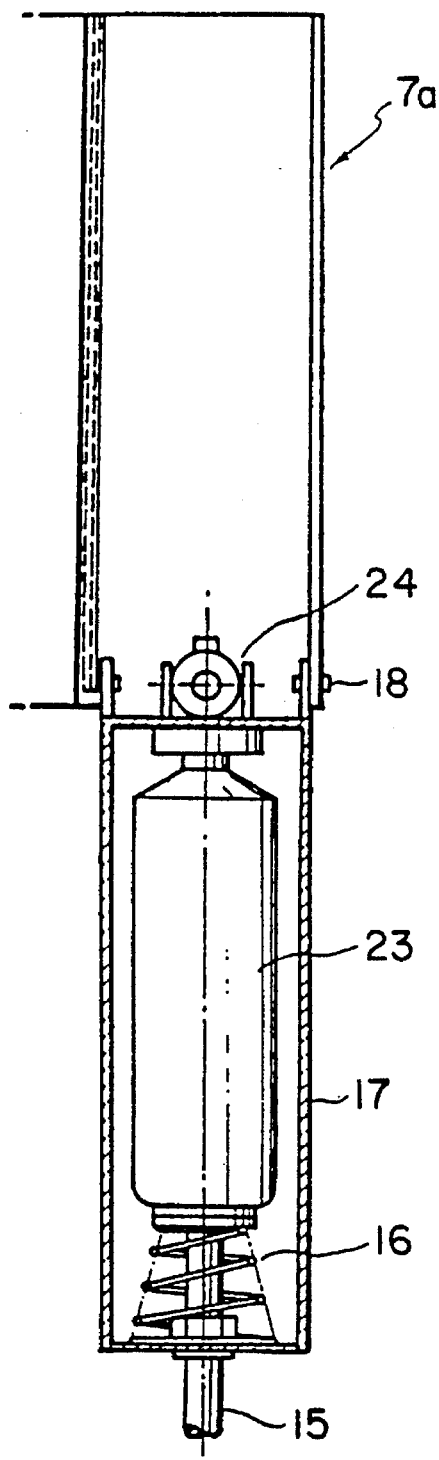
FIG. 2 is a front elevational view of the soap supplier compartment.

Referring to FIG. 2 one of the toiletry set/soap suppliers of the invention is shown. The supplier 7a consists of a container holder 17 which is fixed by a hinge 18 to the supplier 7a. Container holder 17 can thus be rotated for ease of loading, unloading or filling a container 23. A push button or clamp 15 is resiliently fixed by a spring 16 or fixed by a threaded handle, etc. in the upper part of the container holder 17, and a solenoid valve 24 is located below the container 23 for dispensing a preset and desired amount of soap or toiletry contained within the container 23.

Figure 4:
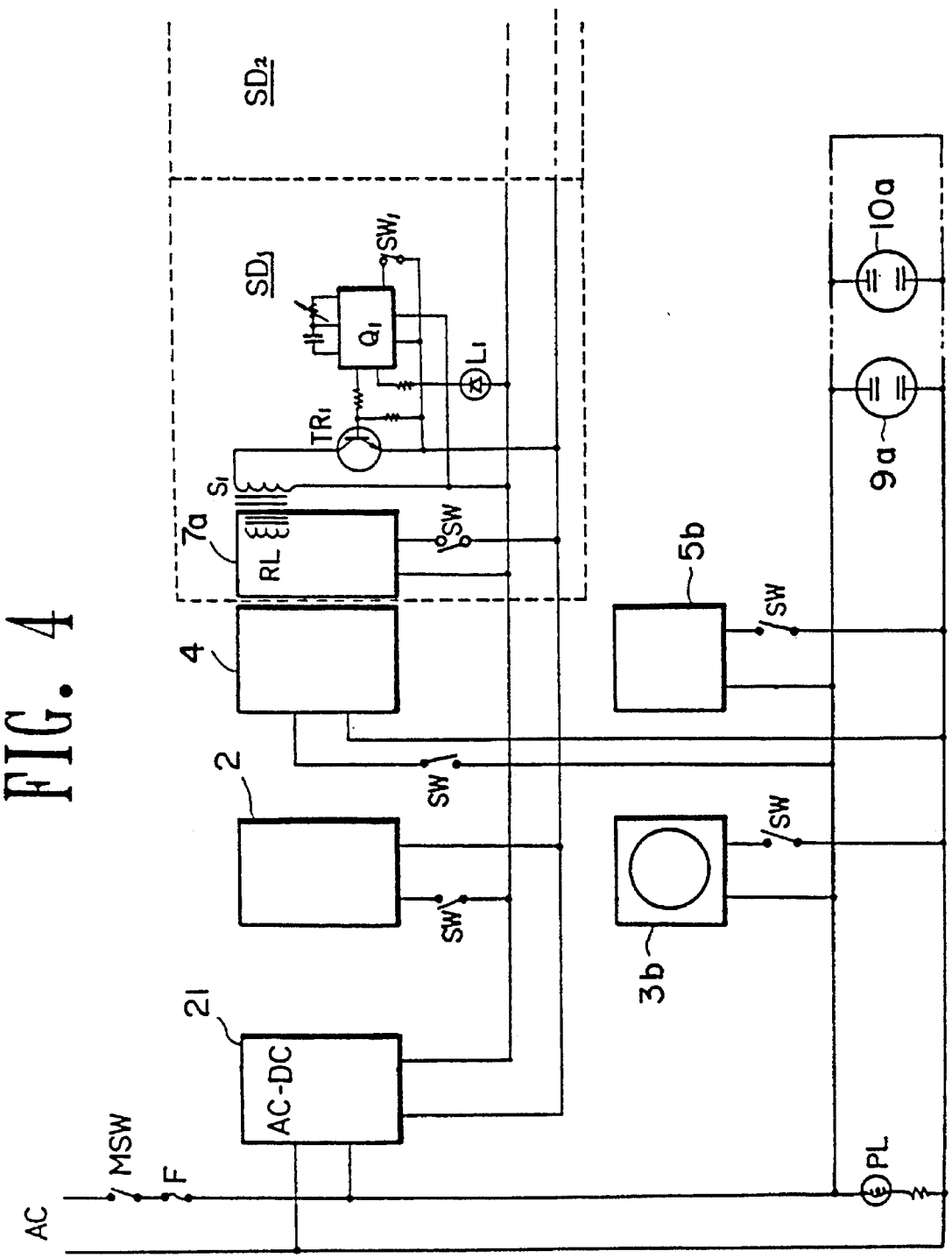
FIG. 4 is an electrical circuit diagram for the restroom organizer.

The central electric control circuit 11 of the automated organizer i is structured as follows referring to FIG. 4: a main switch MSW which controls the electricity of the organizer 1; a lamp PL displays whether the circuit 11 is on or off; an AC-DC converter 21 is built into the control circuit 11; an electric toothpaste dispenser 2 which dispenses a desired amount of toothpaste automatically by inserting the toothbrush into the dispenser (as explained in U.S. Pat. No. 5,050,773 and U.S. Pat. No. 5,215,218 incorporated herein by reference). The toothbrush sterilizer 4 turns off automatically after the sterilizing light 12 has been turned on for a prefixed period of time to sterilize the toothbrush 22 after the toothbrush 22 has been inserted as explained above; electric charging apparatus 3b and 5b for the electric toothbrush and electric razor can also be used as known to one of ordinary skill in the art; 7a is an example of a toiletry set or soap supplier and 7n expresses that multiple sets of the same structure may be added on to the organizer 1.

The solenoid valve circuit SD-SDn of the toilet set and soap supplier 7a–7n is a kind of timer circuit to set up the period of opening and closing time of the solenoid valve S-Sn, and consists of a transistor Tr1, time pulse circuit Q1 switch SW1 and expressing Lamp L1.

When the user turns on one of the switches SW1-SWn of the circuit 11 the selected transistor of TR1-TRn turns on for the pulse period of the selected time pulse circuit of Q1-Qn. Then the selected solenoid valve of S1-Sn operates for that period to dispense the desired amount of toiletry or soap.

In this invention the dispensing of the toiletry and/or soap are controlled by the electrical circuit 11, but the dispensing could also be controlled by a mechanical means (push/pull, etc).

The automated organizer 1 described above does not need an electrical control system for each apparatus and some of the items such as the electric razor 5a will have their own control system.

A user can shave with the electric razor 5a, take the sterilized toothbrush 22 out from the toothbrush sterilizer 4 to obtain a desired amount of toothpaste from the automatic toothpaste dispenser 2 to clean his or her teeth, bathe themselves with soap from the soap supplier 7a by pushing handle 15, then put on lotion or cream from the toiletry supplier 7a-7n and then make up their hair with the hair dryer hanging on hanger hook 8. Therefore, one can make up their body more conveniently and simply while the bathroom space is utilized more effectively.

Figure 5:
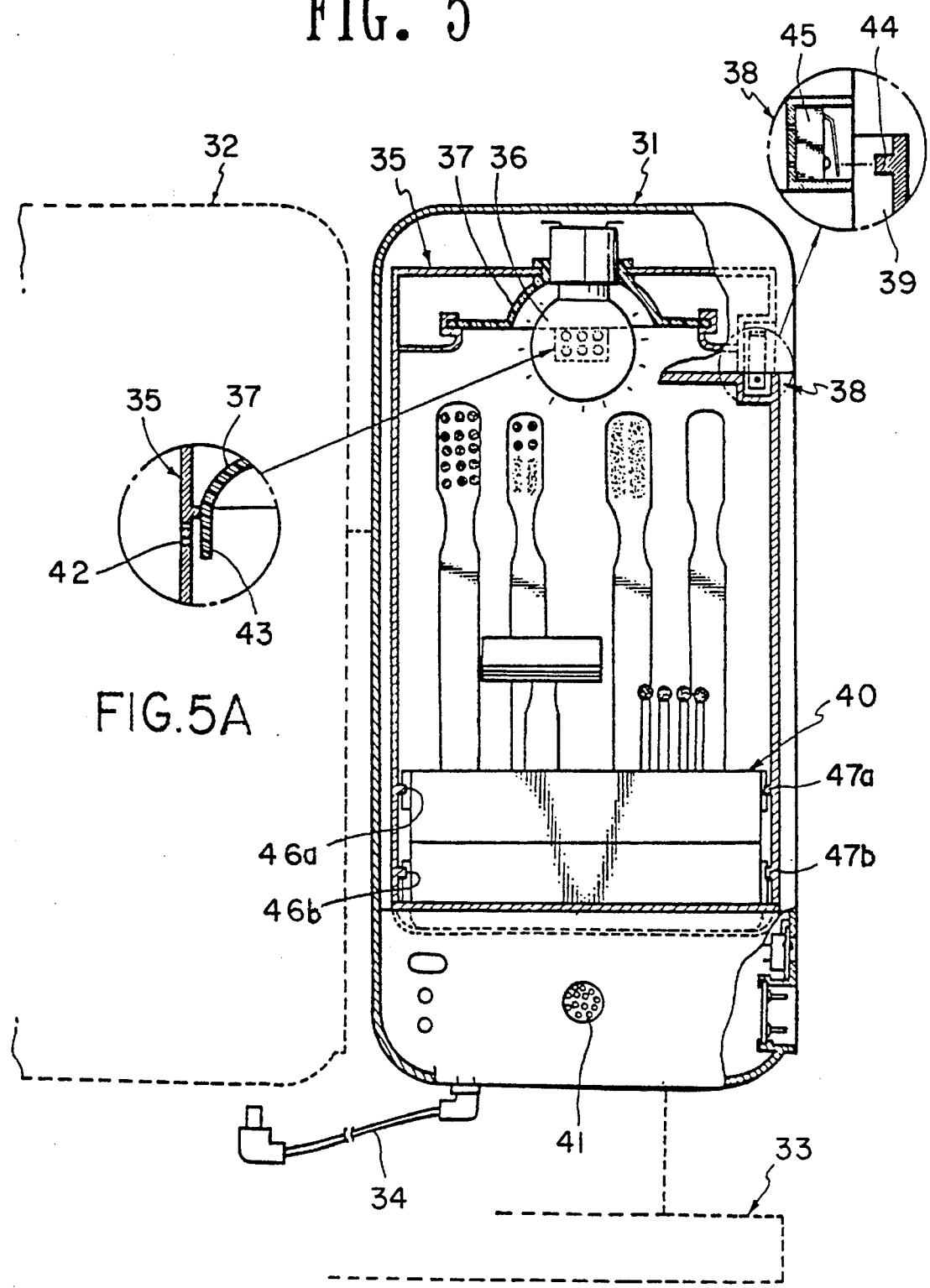
FIG. 5 is a partial section view of a second embodiment of the sterilizer.

Another embodiment of the sterilizer compartment is shown in FIG. 5. The sterilizer 31 is used to sterilize necessities requiring daily sanitation (i.e. toothbrushes, shaving razors, tartar cleaners, ear swabs, baby bottles and nipples for infants).

FIG. 5 shows one example of the sterilizer invention in operation which can be bought as a separate component, together with the toothpaste dispenser 32 or together with the organizer. The sterilizer 31 shown is built as a compartment next to the toothpaste dispenser 32 on the stand 33. The sterilizer 31 is electrically connected to the toothpaste dispenser 32 by the electric wire 34 on the stand 33 so that sterilization of the toothbrush and dispensing of toothpaste can both be carried out conveniently. The stand 33 is optional since the sterilizer 31 and/or the toothbrush dispenser 32 can be wall mounted as well. The sterilizer 31 includes a sterilizing light 36, a reflection mirror 37 and an upper main block 35, a switch 38 mounted on switch mounting block 45 located on the main block 35 and the door 39 which regulates the sterilization light 36 and the music circuit 41. A storage case 40 is placed below the sterilization light 36 in the main block 35 and can be rotated forward and backward. An electric circuit shown in FIG. 16 turns the sterilization light 36 and the music system 41 on and off periodically. The reflection mirror 37 extends or connects to an ultraviolet ray blocking plate 43. Ventilation holes 42 are located in the main block 35 behind the ultraviolet ray blocking plate 43 to prevent the ultraviolet rays of light from reflecting out of the main block 35 while moisture contained within the main block can vent through the ventilation holes 42.

A small switch 38 such as a micro switch is equipped in the main block 35 and can be tripped by a prong 44 located on the door 39. The electric circuit will be off when the door 39 is open as shown in FIG. 5. The switch system also acts as a safety feature to prevent the user from being exposed to harmful ultraviolet rays which would occur if the sterilization light 36 remained on while the door 39 is open.

Figure 6:
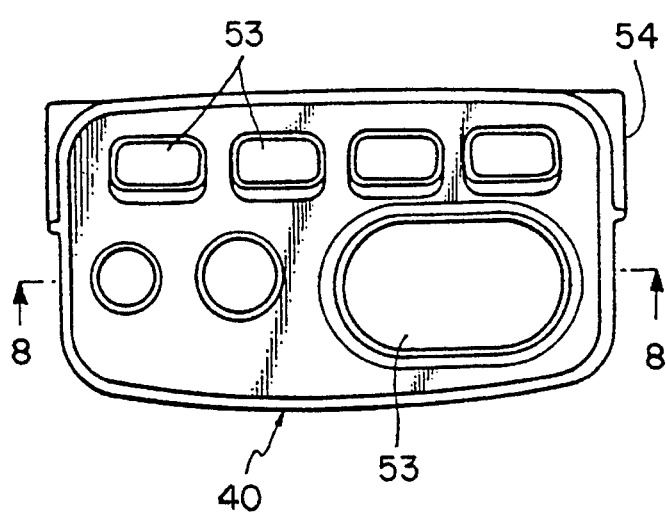
FIG. 6 is a top view of the storage case.
Figure 7:
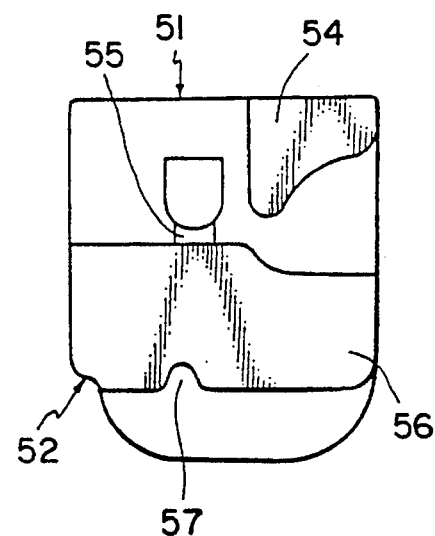
FIG. 7 is a right side view of the storage case.
Figure 8:
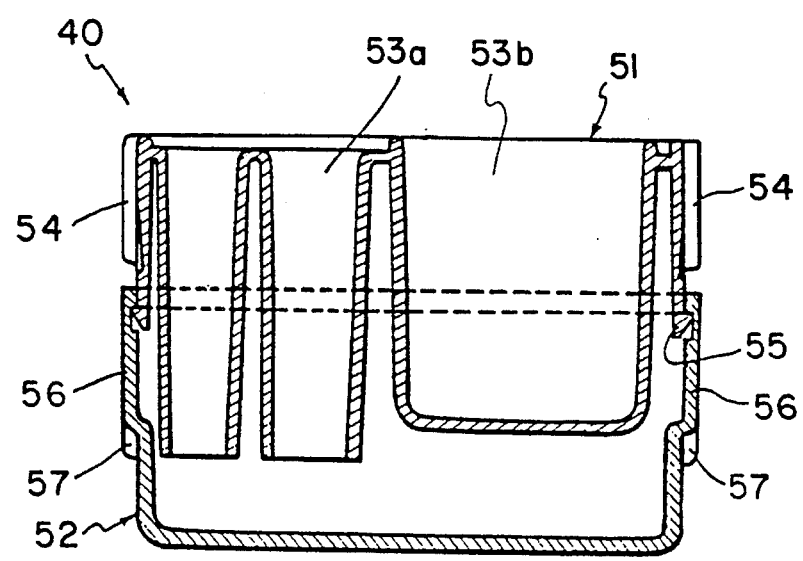
FIG. 8 is a sectional view taken along line 8—8 of FIG. 6.

Referring to FIGS. 6–8 the storage case 40 consists of a main body 51 and a housing 52 which can be fixed to snap to the lower part of the main body 51. The housing 52 is designed to hold water dripping from storage compartments 53. Housing or water tray 52 can be easily removed from main body 51 and both parts may be rinsed or cleaned.

Storage compartments 53a and 53b are designed to store toothbrushes, razors, tooth tarter cleaners, ear swabs, etc., in the main body 51.

With the housing 52 snapped to the main body 51 with a holding plate 55 and a first retainer 54 formed at both sides of the main body 51, the storage case 40 can be set up in the main block 35 on the hinge axles 46a, 47a (FIG. 5). The notch 57 of the second retainer 56 on both sides of the housing 52 fits over the hinge axles 46b, 47b of the main block 35.

Figure 9:
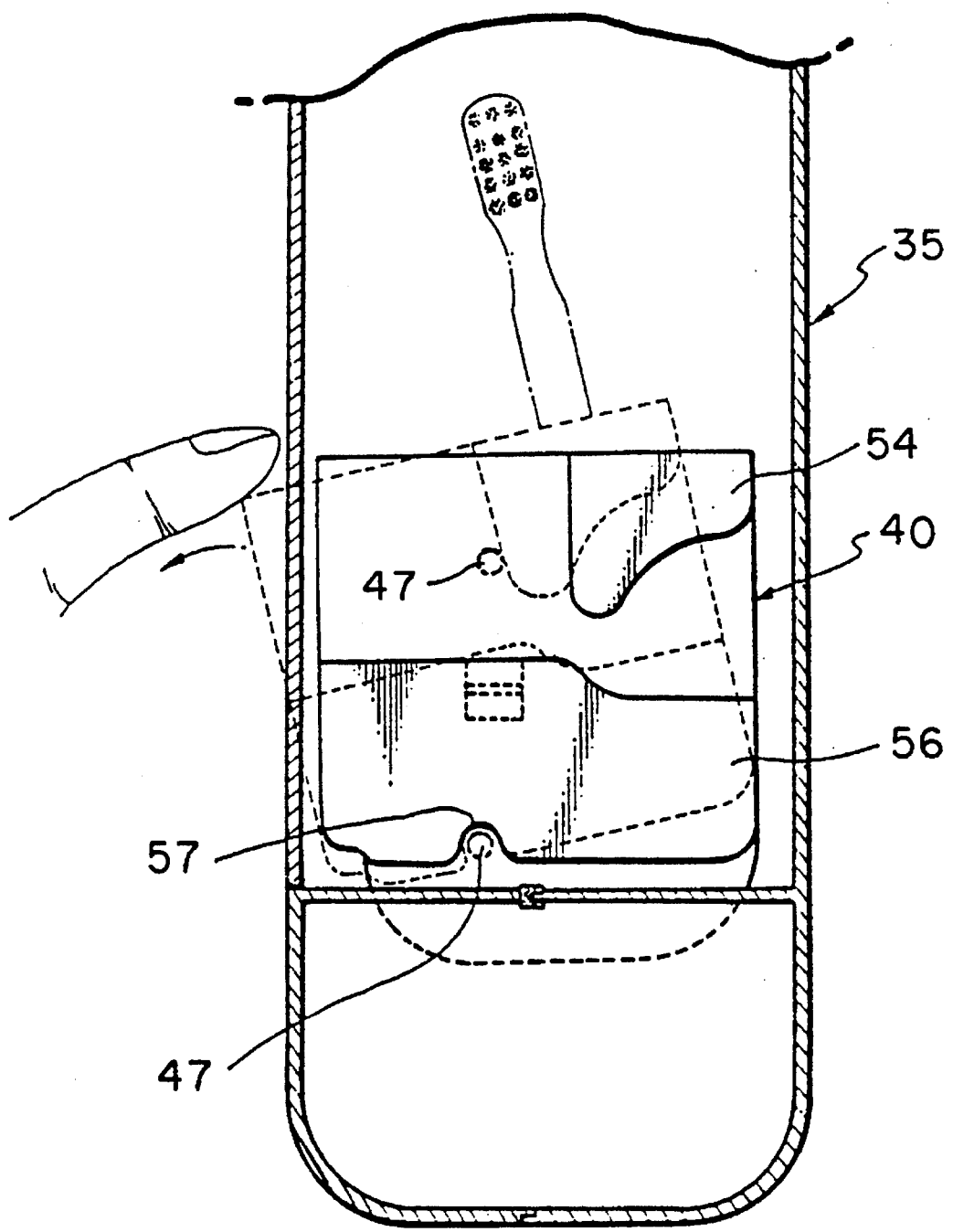
FIG. 9 is a partial section view of the storage case in use.

The storage case 40 can be set off from the vertical in the main block 35 since the pair of hinge axles 46a and b, 47a and b and the main block 35 allows the storage case 40 to rotate forward and backward as shown in FIG. 9.

The first retainers 54 on both sides of the storage case 40 prevent the storage case 40 from overturning along the axis of the hinge axles 46b, 47b on the notches 57.

A user should pull the storage case 40 for tilting it around the notches 57 fitting hinges 46b, 47b The storage case 40 can also be designed to fall forward automatically if the notches 57 and fitting hinges 46b, 47b are formed in the back part of the case 40.

Figure 10:
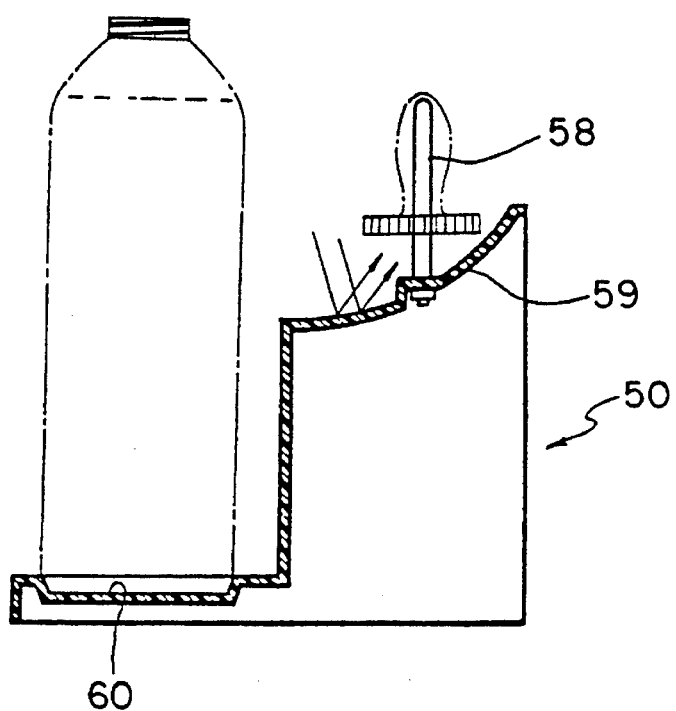
FIG. 10 is a partial section view of another embodiment of the storage case.

FIG. 10 shows another storage case 50 embodiment in use. If necessary the storage case 40 shown in FIGS. 6–9 can be removed from the main block 35 and the other storage case 50 for holding a nipple and a milk bottle for an infant can be inserted for sterilization of these articles. A holding bar 58 in the middle of the reflection plate 59 holds a nipple to be sterilized both on the inside and the outside of the nipple and a recessed seat 60 holds a milk bottle at a lower part of the case 50.

Figure 10A:
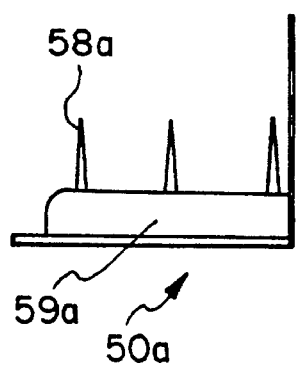
FIG. 10A is a side view of another storage case embodiment.

FIG. 10a shows another embodiment of a storage case 50a which can be mounted on prongs (not shown) within the main block 35. The storage case 50a functions as a shelf upon which a bottle or other article can be placed. A reflection plate 59a can also be placed on the storage case 50a. Reflection plate 59a includes holding bars 58a for the mounting of nipples or other articles. Reflection plates 59 and 59a may be made of chrome or some other material which promotes the reflection of light for sterilizing on the inside and outside of articles such as nipples.

FIGS. 12–18 show another embodiment of the sterilizer in operation. The sterilizer 70 is built in combination with the electric toothpaste dispenser 60 which is described in U.S. Pat. No. 5,050,773 and U.S. Pat. No. 5,215,218, both incorporated herein by reference. This toothpaste dispenser 70 includes a motor assembly 71, an elevator assembly 72, a roller assembly 73, which is ascended and descended by the elevator assembly 72, a tube grasping assembly 74 for holding the nozzle of the toothpaste tube 75 and a toothpaste dispensing assembly 76 (a more detailed explanation of the operation of the dispenser and the structure of the dispenser are described in the above listed U.S. Patent and Application). Cover 77 rotates about hinge 79 to allow access to and replacement of toothpaste tube 75. Door assembly 81 is hinged to rotate at axle 83 of the toothpaste dispenser 70.

Figure 14:
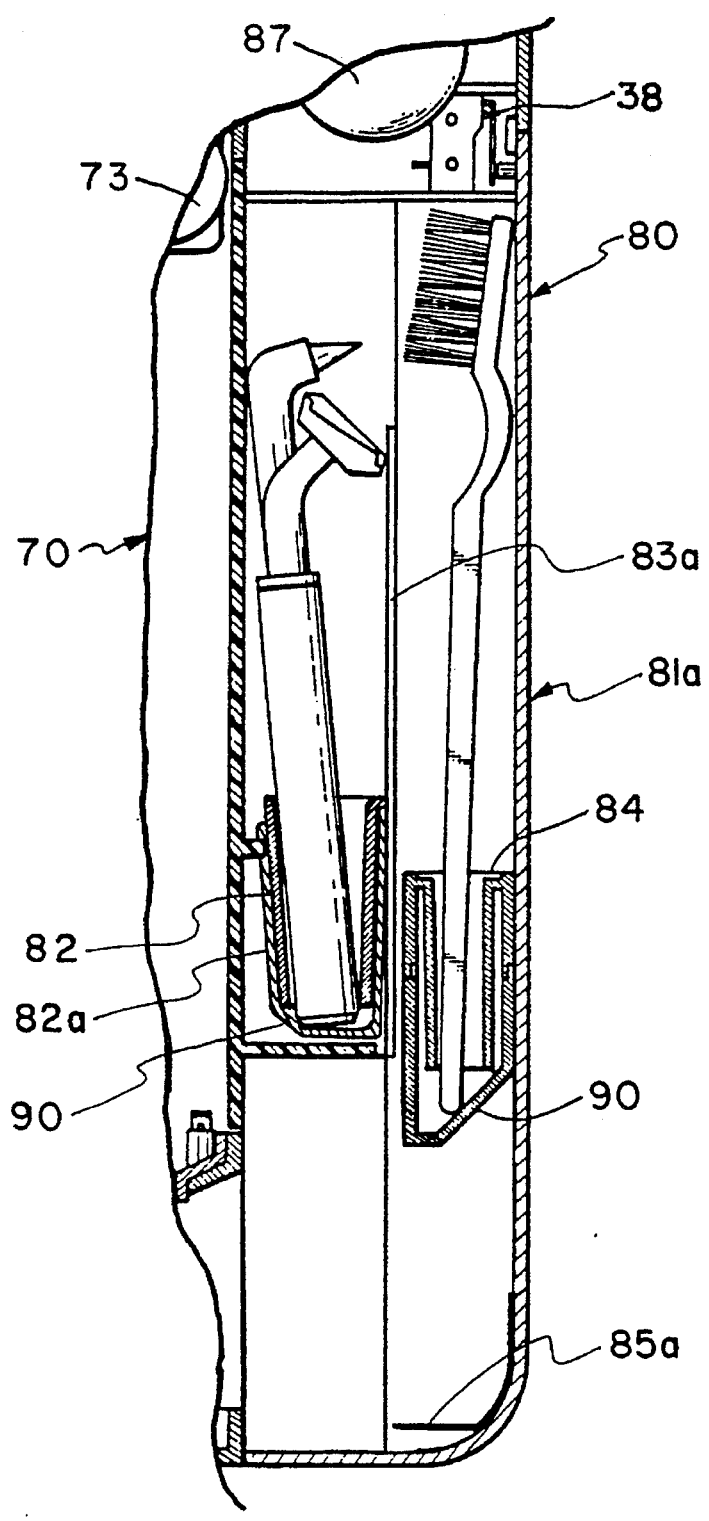
FIG. 14 is an enlarged partial section view of another tray mount option to that shown in FIG. 13.
Figure 15:
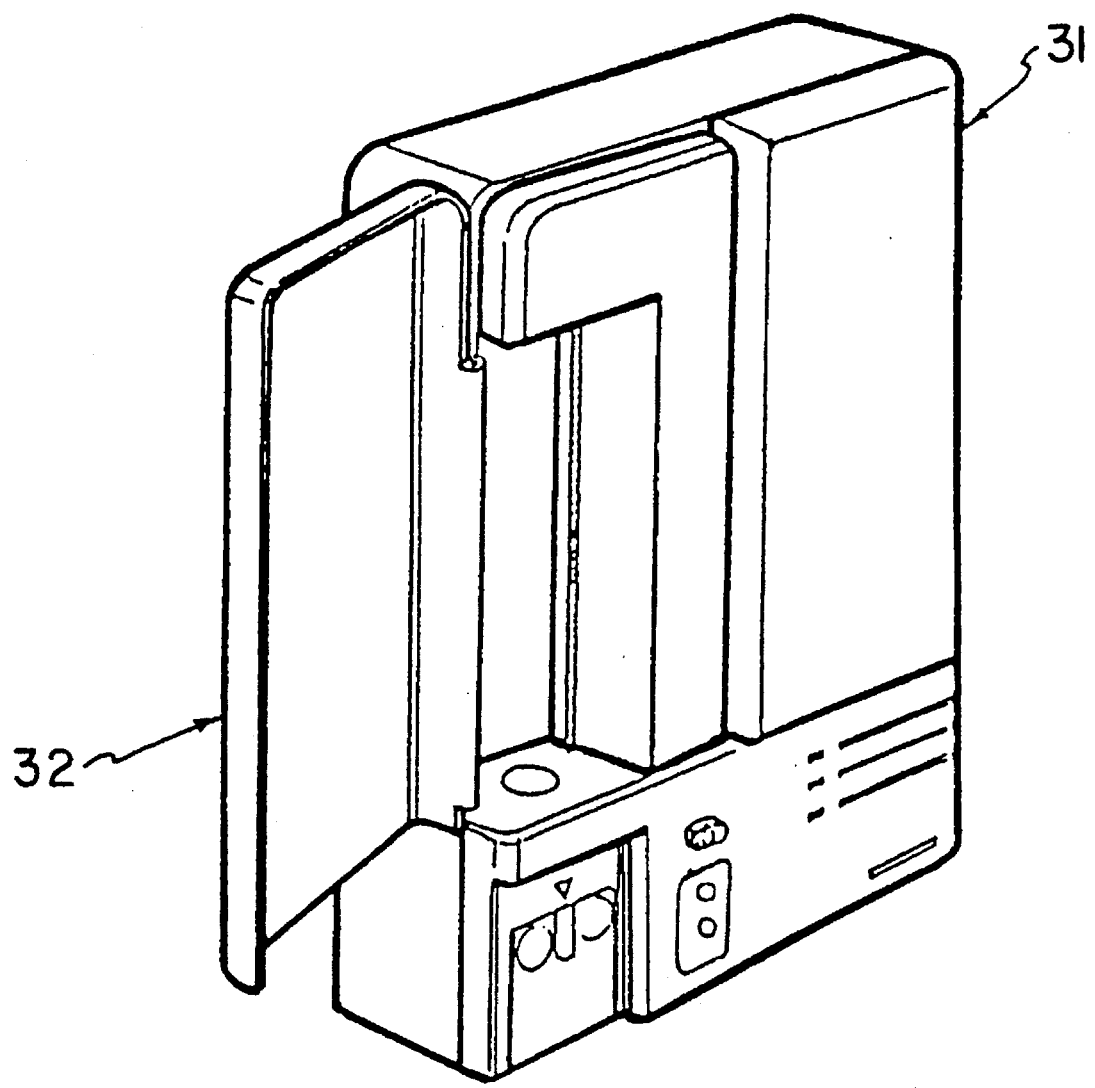
FIG. 15 a perspective view of FIG. 1.

In the embodiment of the invention shown in FIG. 14, the sterilizer 80 is built in the door assembly 81a or front portion of the toothpaste dispenser 70. An upper storage compartment 82 is attached or clipped to the backside of the toothpaste replacement door assembly 81a of the toothpaste dispenser 70 for effective utilization of space such that the dispenser 70 and the sterilizer 80 can be harmonized together. The door assembly 81a is hinged to rotate on hinge axle 83a of the toothpaste dispenser 70. Door assembly 81a includes a ledge 85a which can be used for a cup or other article. Upper storage compartment 82 and lower storage compartment 84 can be hung on prongs or ledges molded in to the door assembly 81a or against the toothpaste dispenser 70. The storage compartments 82 and 84 can be designed in a variety of fashions. For instance storage compartment 82 includes a drip cup 82a which can be disconnected from the compartment 82 for cleaning.

Figure 12:
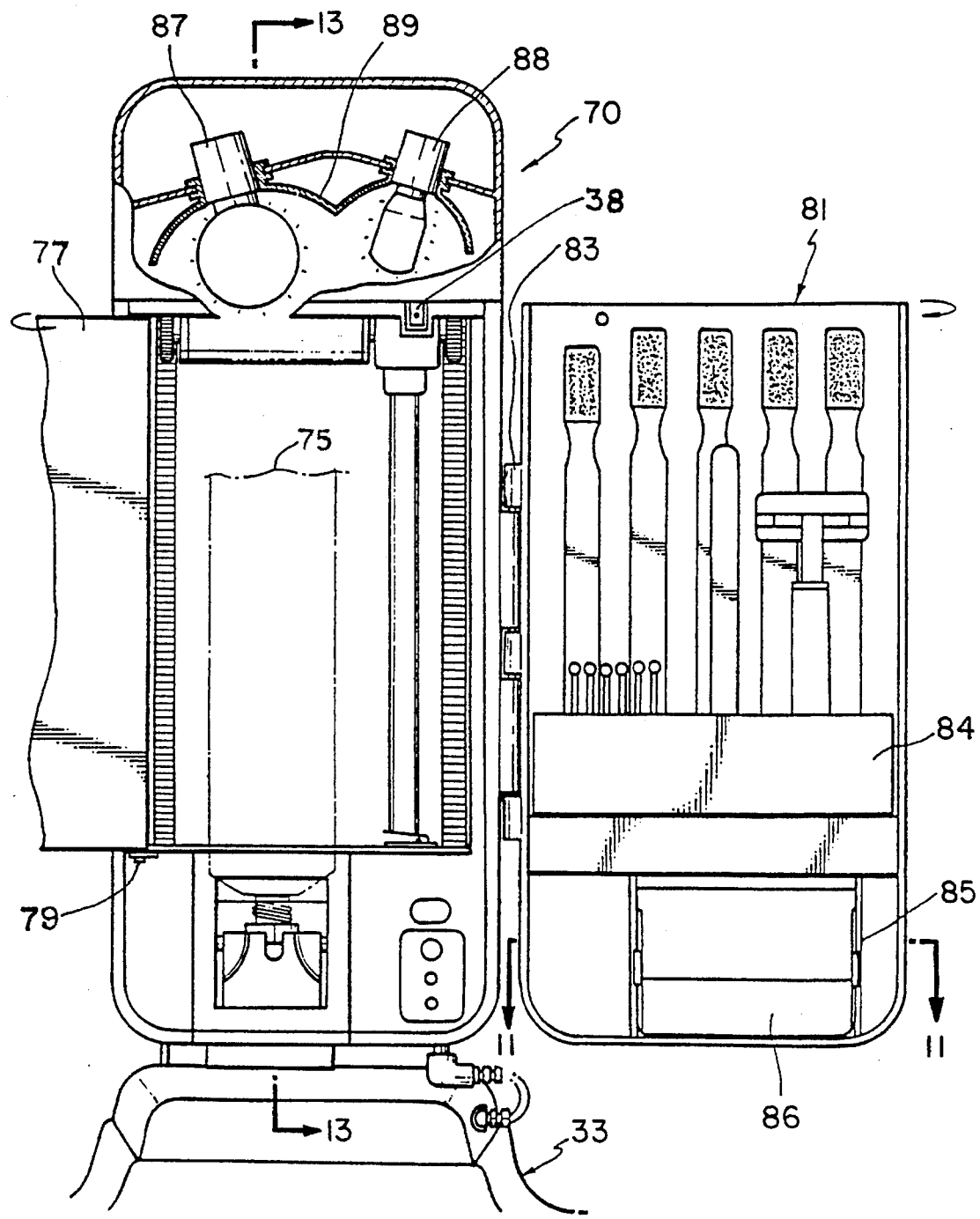
FIG. 12 is a front view of another embodiment of the invention combining the sterilizer as a built in feature on the front door of a toothpaste dispenser.
Figure 13:
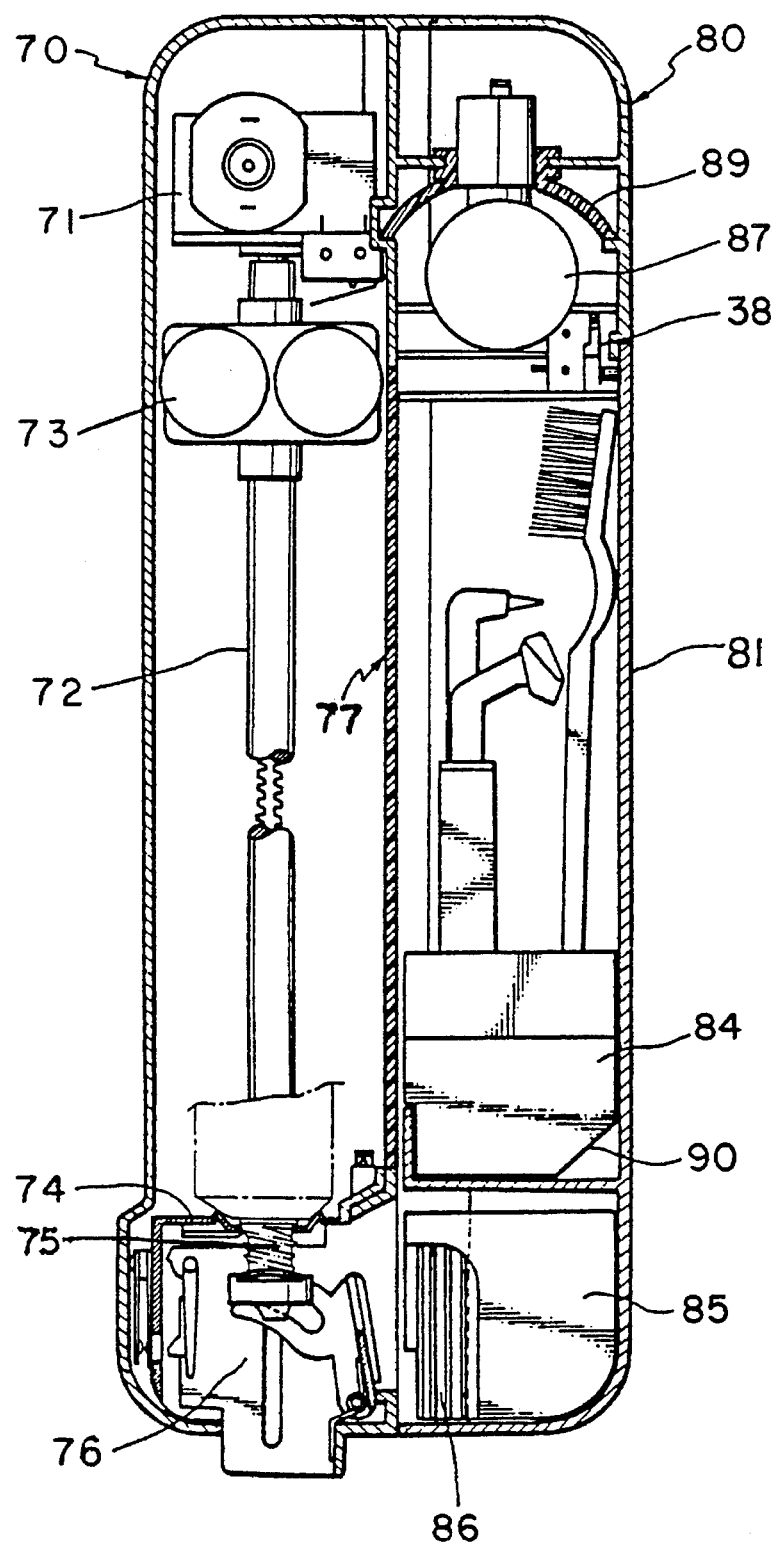
FIG. 13 is a sectional view taken along line 13—13 of FIG. 12.

An ultraviolet light 87 with a reflection mirror 89 and an optional heating lamp 88 for elevating temperatures or drying are built into the upper portion of the sterilizer 80 as seen in FIG. 12. A lower storage case 84 and a cup 86 are mounted in the lower portion of the sterilizer 80.

Figure 11:
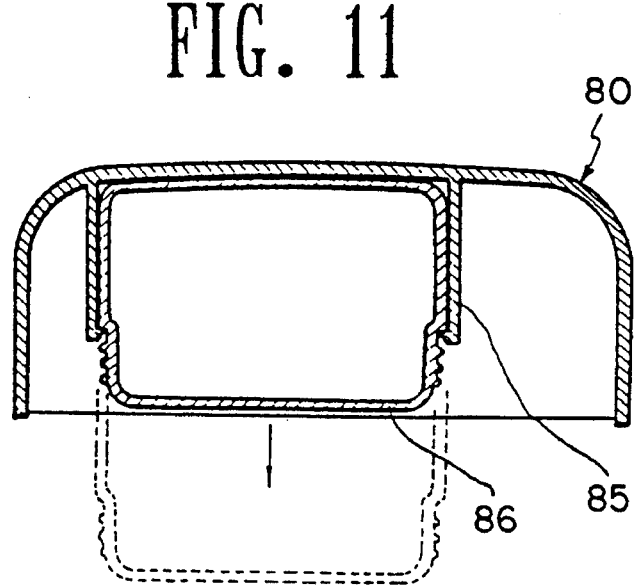
FIG. 11 is a sectional view taken along line 11—11 of FIG. 12.

The bottom 90 of storage case 84 is formed with a slanted or declined surface 90 as shown in FIG. 14 so that one end of the stored item (such as a toothbrush) will be slanted from the vertical against the wall for maximum exposure of the item to direct ultraviolet rays. The cup 86 can be snapped into the cup holder prongs 85 as shown in FIG. 11.

The sterilizer 31 or 80 of this embodiment of the invention can be mounted next to the toothpaste dispenser 70 or built in combination with the dispenser 70.

A user can take out the sanitized and dried objects by opening the door 39 or opening the door assembly 81 and can dispense toothpaste from the electric dispenser 32, 70 automatically and conveniently. Milk bottles or other miscellaneous items can be sanitized more readily by changing storage cases.

Figure 16:
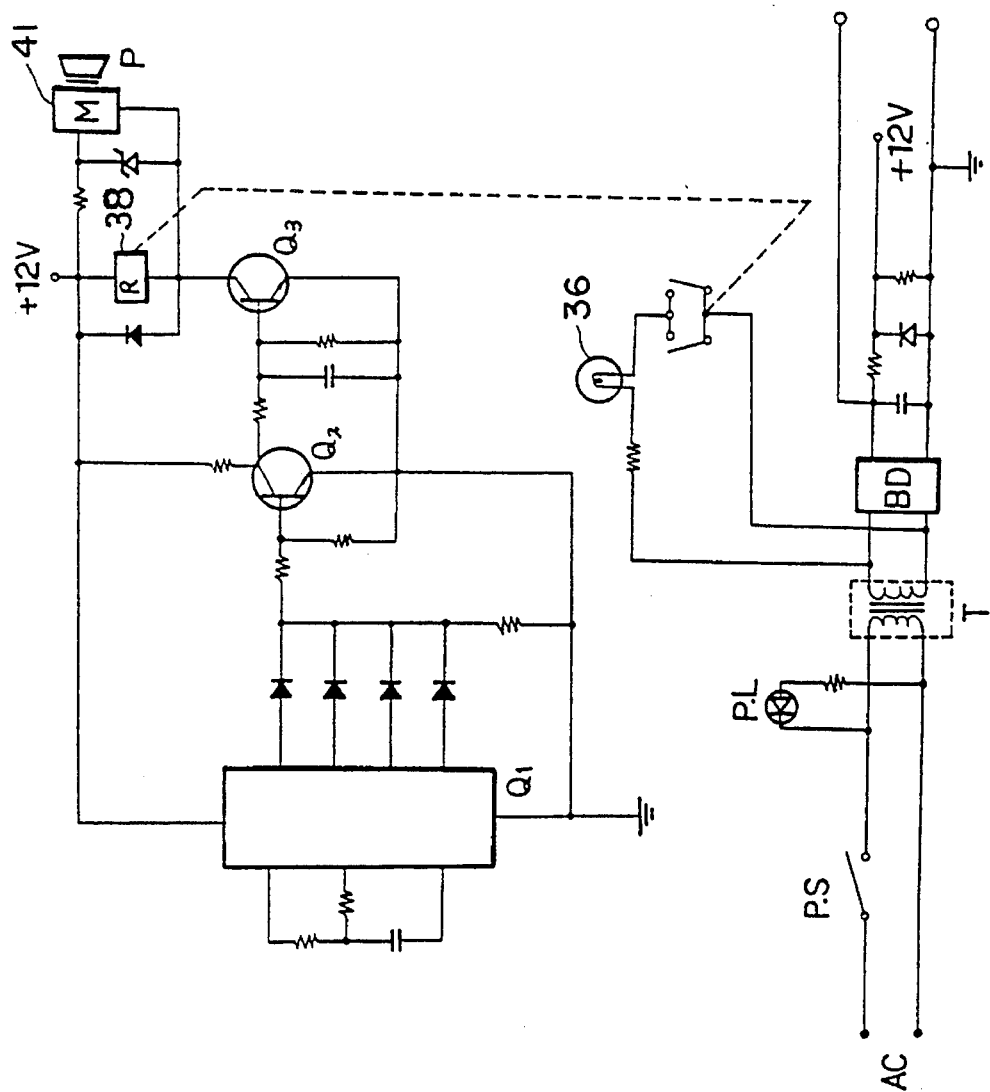
FIG. 16 is the electrical circuit diagram of the sterilizing light and the music box of the sterilizer.

Referring to FIG. 16 the electric circuit of the sterilization light 36 and music system 41 of the sterilizer is shown. PS is a switch at the electric source; PL is a ! amp showing whether the electric connection is on or off; T is a transformer converting AC to DC; BD is a bridge diode, 36 is a sterilization light; R is a relay switch 38 which turns off when the door 81 is opened and turns on when the door 81 is closed; 41 is a music circuit M with a music phone P; Q1 is a pulse counter and pulse circuit counting pulses repeating and creating periodic pulses such as the periodic pulse circuit which creates a pulse for two minutes to the sterilizer every 30 minutes; and Q2, Q3 are switching transistors to convert the relay switch 38 on and off.

The operation of the electric circuit is as follows:

When the sterilizer of this invention is operated, in other words, when the door is closed, and the relay circuit is at "On" position and the AC electric source is at "On" position, the lamp PL showing the electric connection turns on, then the electricity is supplied through the transformer T to the sterilizing light 36 and melody circuit 41 to turn on. Meanwhile, DC 12 volt electricity is supplied through the DC 13V rectifier bridge circuit BD. Electricity is supplied to the pulse counter, pulse circuit Q and pre-set periodic pulse for example for two minutes, and the transistor Q1, Q2 turns off after they are at "On" position for the two minute period. Also, the relay 38 is turned off and electricity is disconnected to turn off the light 36 and the melody 41.

The sterilizing light 36 and music 41 turn on again for the pulse period (2 minutes) after counting the preset period (for example 30 minutes), and the above described activity is repeated again.

Meanwhile, when the user opens the door 39 while the sterilization light 36 and music 41 are being operated, the relay or switch 38 turns off and the sterilization light 36 and music 41 turn off. When the door 39 is closed the sterilization light 36 and the music 41 are operated periodically, for example, repeatedly for two minutes every 30 minutes.

Figure 17:
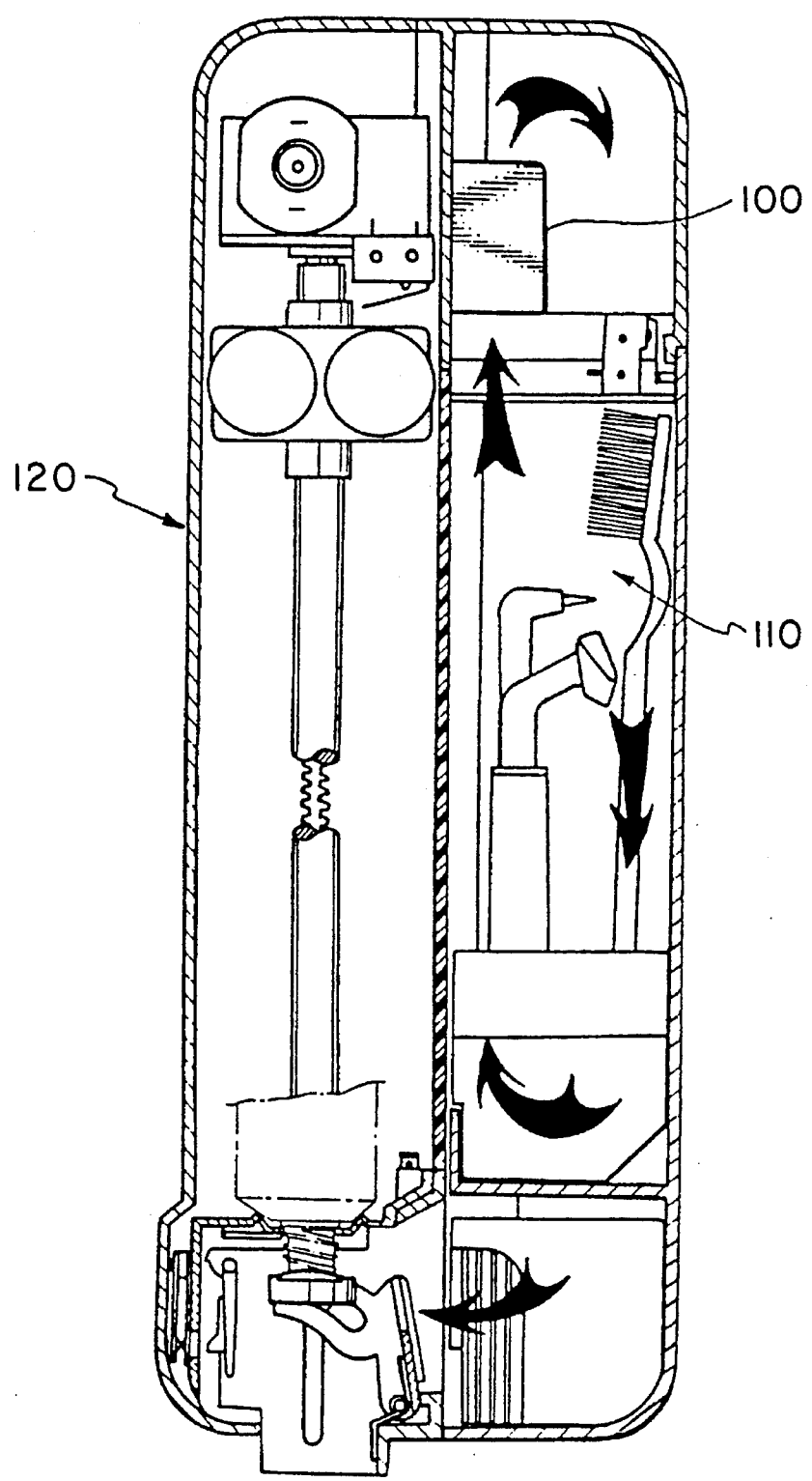
FIG. 17 is a side cross sectional of another sterilizer embodiment, the ozone sterilizing apparatus.

Referring to FIG. 17 an example of an ozone device 100 built into the storage compartment 110 of an electric toothpaste dispenser 120 is shown. Details of the electric toothpaste dispenser are described in U.S. Pat. No. 5,050,773 and U.S. Pat. No. 5,215,218, both incorporated herein by reference and details of the storage compartment 110 are described above with the ozone apparatus 100 replacing ultraviolet lighting.

Referring to FIG. 19 the ozone apparatus 100 consists of a pair of catalyst filters 102, 103, a ceramic electrode 104 placed between the filters 102, 103 and a fan 105. The ozone atmosphere is created by the electric discharge between the ceramic electrodes 104. The fan 105 then pulls the ozone atmosphere through the system to sterilize the toothbrushes and other articles, including the nozzle of the toothpaste tube. The ozone apparatus sucks polluted air in the toothbrush storage room 110 or in the toothpaste dispenser 120 by the fan 105. Oxidation is created by high voltage electric discharge between the ceramic electrodes 104. The ozone destroys foul odors, germs, etc. Ozone, $O_3$, is produced when an electric spark is passed through air or oxygen. Ozone is a powerful oxidizing agent which can be used for sterilization to disinfect and deodorize air, water, and surfaces requiring disinfection and deodorization. During disinfection and deodorization the ozone is converted to oxygen containing polluted air which circulates back to the ozone apparatus 100 for re-oxidation. Therefore, the ozone apparatus 100 keeps the entire system clean.

Figure 18:
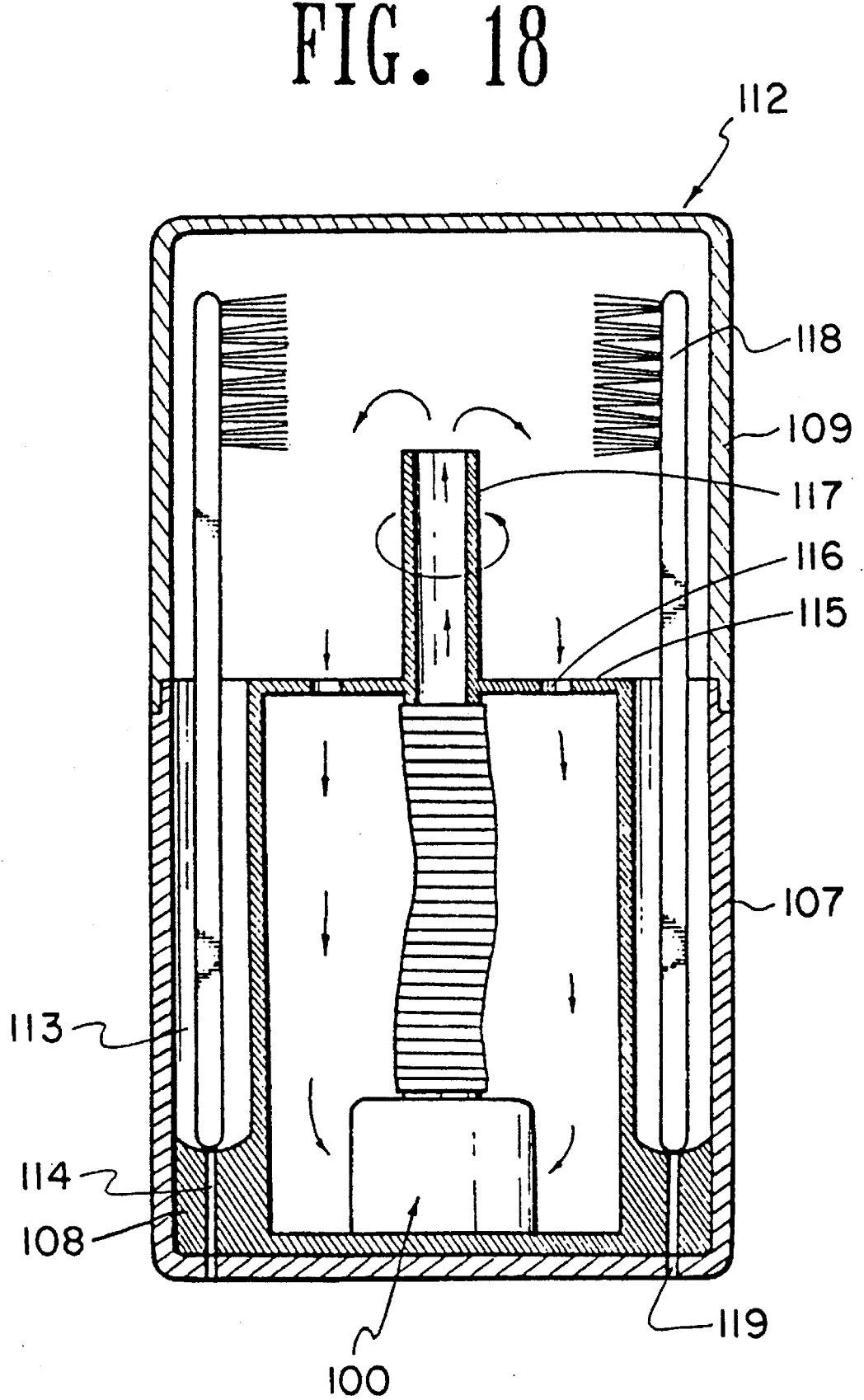
FIG. 18 is a cross sectional view of another embodiment of the toothbrush ozone sterilizing apparatus.

FIG. 18. shows another embodiment of the ozone sterilizing apparatus with the ozone apparatus 100 built inside the toothbrush storage room 112. The toothbrush storage room 112 consists of an outside canister 107, a rotatable inner canister 108, and a cover 109. The ozone apparatus 100 is built and attached inside the inner canister 108. The inner canister 108 has molded toothbrush storage compartments 113, drainage ducts 114, and end wall 115 with atmosphere return openings 116 and an ozone feed tube 117 for circulation within the toothbrush storage room 112 and the inner canister 108. In this manner the ozone apparatus sterilizes harmful microbes on toothbrushes 118 stored in the storage room 112 while disinfecting and deodorizing the atmosphere inside of the storage room 112 and inner canister 108. The outside canister 107 includes passages 119 so that the molded toothbrush storage compartments 113 can drain through ducts 114 and passages 119.

The preferred embodiment of this invention has been shown and described above. It is to be understood that minor changes in the details, construction and arrangement of the parts may me made without departing from the spirit or scope of the invention as claimed.

I claim:

1. A sterilization apparatus, comprising:

a main block;

a means for sterilization attached within the main block wherein said sterilization means comprises an ultraviolet light;

a reflection surface connected within the main block;

a means for controlling said sterilization means; and a removable storage case mounted within said main block, having a main body which defines at least two storage compartments and having a means for holding water dripping from the storage compartments which fits over said main body.

2. The sterilization apparatus according to claim 1 wherein said sterilization apparatus further includes a heat lamp mounted within the main block.

3. The sterilization apparatus according to claim 1 wherein said means for controlling said sterilization means includes a means for repeatedly turning on said sterilization means for a preset period after a preset interval has passed.

4. The sterilization apparatus according to claim 1 wherein said removable storage case includes a bottom having a surface slanted from the vertical.

5. A sterilization apparatus, comprising:

a main block;

a means for sterilization attached within the main block;

a means for controlling said sterilization means;

a removable storage case mounted within said main block; and an electric toothpaste dispenser connected to the main block.

6. The sterilization apparatus according to claim 5 wherein said sterilization means comprises an ozone apparatus.

7. The sterilization apparatus according to claim 6 wherein said ozone apparatus includes a pair of catalyst filters where one of said catalyst filters is located before a ceramic electrode and the other of said catalyst filters is located after said ceramic electrode and a fan located on one end of one of said catalyst filters.

8. The sterilization apparatus according to claim 5 wherein said sterilization means comprises an ultraviolet light.

9. The sterilization apparatus according to claim 5 wherein said sterilization apparatus further includes a heat lamp mounted within the main block.

10. The sterilization apparatus according to claim 15 further including a soap supplier mounted proximate said sterilization apparatus and a central electric control circuit mounted proximate said soap supplier for controlling said sterilization apparatus, said electric toothpaste dispenser and said soap supplier.

11. The sterilization apparatus according to claim 5 wherein said means for controlling said sterilization means includes a means for repeatedly turning on said sterilization means for a preset period after a preset interval has passed.

12. The sterilization apparatus according to claim 5 wherein said removable storage case includes a bottom having a surface slanted from the vertical.

13. The sterilization apparatus according to claim 5 wherein said removable storage case includes a main body which defines at least two storage compartments and having a means for holding water dripping from the storage compartments which fits over said main body.

14. A sterilization apparatus, comprising:

a main block;

a means for sterilization attached within the main block;

a means for controlling said sterilization means including a means for repeatedly turning on said sterilization means for a preset period after a preset interval has passed; and a removable storage case mounted within said main block having a main body which defines at least two storage compartments and having a means for holding water dripping from the storage compartments which fits over said main body.

15. The sterilization apparatus according to claim 14 wherein said sterilization means comprises an ultraviolet light.

16. The sterilization apparatus according to claim 14 wherein said sterilization apparatus further includes a heat lamp mounted within the main block.

17. The sterilization apparatus according to claim 14 wherein said removable storage case includes a bottom having a surface slanted from the vertical.

\* \* \* \* \*